United States Patent [19]
Stern et al.

[11] Patent Number: 5,187,815
[45] Date of Patent: Feb. 23, 1993

[54] NEEDLESTICK PROTECTIVE GLOVE

[75] Inventors: Joseph A. Stern, Hampton; Stephen L. Green, Newport News; Charles B. King, Hampton, all of Va.; Sharon B. May, San Antonio, Tex.

[73] Assignee: Medev Corporation, Newport News, Va.

[21] Appl. No.: 542,873

[22] Filed: Jun. 25, 1990

Related U.S. Application Data

[63] Continuation-in-part of Ser. No. 289,246, Dec. 23, 1988, Pat. No. 4,942,626.

[51] Int. Cl.$^5$ ............................................. A41D 19/00
[52] U.S. Cl. ..................................... 2/161 R; 2/164; 2/167
[58] Field of Search .............. D2/159, 161 R, 163, D2/167, 168, 20, 21

[56] References Cited

U.S. PATENT DOCUMENTS

| Re. 31,538 | 3/1984 | Antonious | 2/161 A |
|---|---|---|---|
| 2,309,476 | 1/1943 | Patterson, Jr. | 2/161 A |
| 4,272,849 | 6/1981 | Thurston et al. | 2/161 R X |
| 4,275,812 | 6/1981 | Poncy et al. | 2/161 R X |
| 4,399,567 | 8/1983 | Weon Joong | 2/161 R |
| 4,416,026 | 11/1983 | Smith | 2/161 R |
| 4,942,626 | 7/1990 | Stern et al. | 2/163 X |

Primary Examiner—Peter Nerbun
Assistant Examiner—Sara M. Current
Attorney, Agent, or Firm—Larson and Taylor

[57] ABSTRACT

A glove for use by medical personnel which is adapted to help prevent accidental injuries when handling needles includes a first discrete layer of flexible material which has a pore size smaller than the diameter of a needle. The first layer forms a glove with an optional opening in the fingerprint area of the index finger stall and middle finger stall. The glove also includes a second discrete layer of flexible material which also has a pore size which is smaller than the diameter of a needle. This second layer is permanently attached to selected areas of the first layer. The selected areas comprise all of the thumb stall, and lateral sides of the index finger stall and middle finger stall. Preferably, the fingernail region is not covered by the second layer and backsides of the first distal joint portion of the index and middle finger stall are covered. A V-opening for the back side of the glove includes two distinct fastening devices. A third discrete layer of corrugated metal foil is optionally provided in the selected areas. Methods for sterilization and disinfecting are also provided.

30 Claims, 3 Drawing Sheets

NEEDLESTICK PROTECTIVE GLOVE

This is a continuation-in-part of application Ser. No. 289,246 filed Dec. 23, 1988, now U.S. Pat. No. 4,942,626.

BACKGROUND OF THE INVENTION

The present invention relates to a protective glove for medical personnel designed to prevent the wearer from accidentally penetrating his or her skin when handling needles. More particularly, the present invention relates to a glove for medical personnel which provides protection from needles and, at the same time, does not significantly interfere with their use of their hands.

Accidents occur when medical personnel are handling needles and particularly when medical personnel attempt to resheath the needle after use. Accidents have occurred whereby the needle enters the sheath at an angle, penetrates the plastic sheath and pricks the user. Also, accidents occur when the needle misses the sheath entirely and sticks the sides of the finger, the thumb or the snuff-box region of the hand.

Needle-handling injuries are particularly dangerous to medical personnel who run the risk of exposure to disease. Highly communicable diseases such as hepatitis-B, and AIDS have caused serious concern to medical personnel treating patients affected by these diseases. Each of these diseases can be communicated to medical personnel as a result of an accidental injury when handling a contaminated needle which has been used to take blood samples or administer intravenous liquids to a patient.

Typically, an intravenous therapy nurse must locate a suitable blood vessel in a patient's limb, normally the arm, by palpating the body part. This requires maximum tactility at the fingerprint area of the index and middle fingers of the nurse in order to locate a suitable blood vessel. Upon location of the blood vessel, the nurse inserts a hypodermic needle through the skin into the vessel to inject a fluid or withdraw the patient's blood which, in either case, contaminates the needle. Once the procedure is complete, the needle is generally resheathed and discarded.

Needlestick protection for surgeon's glove is also needed to protect the wearer against accidental needlestick. Fifty-three percent of all needlestick injuries to surgeons involve the index finger of the non-dominant hand. Two hundred and two (202) surgeons, working in the New York City metropolitan area were surveyed as to the frequency of needlesticks during performance of surgery. One hundred seventy-three (173), or 86%, of the surgeons reported at least one puncture injury in the preceding year. Twenty-five percent of the surgeons sustained yearly injury rates of nine or more during per 1,000 operating room hours.

A present method of providing hand protection is the surgeon's sterile latex glove which prevents contact with the patient's body fluids and provides a sterile membrane to protect the patient from contamination by the surgeon. By intention, the thickness of the latex glove is minimal to assure tactility of the wearer. This is especially important since in many cases the operation's success is dependent on the surgeon's ability to feel the patient's organs. The latex offers no real protection from accidental needlestick or from needle burn wherein the needle accidentally drags across the latex glove and cuts through the glove wall. Two pairs of latex gloves are being worn in many instances and is referred to as double gloving.

A more recent glove protection development for surgeons is a metal mesh glove such as the ARMOR-TOUCH glove. The metal mesh glove is worn over top of a latex glove and is then covered by a second latex glove. The metal mesh glove provides protection against accidental cutting from surgical blades. However, it does not provide puncture protection from the tip of a No. 11 blade or from needlesticks, and needlesticks are the most common danger for the surgical team.

Another recently developed surgeon's glove "BI-OSURG" is knitted of stainless steel filaments and worn in the same arrangement as the metal mesh glove, between latex gloves on the hand. Although the glove is tightly knitted, needlestick protection is limited by the openings of the knit pattern.

Yet another glove recently developed for the surgeon which is knitted of polyethylene fibers is VIGARD developed by Allied Signal Incorporated The polyethylene fiber knitted glove is worn by surgeon and covered by a sterile latex glove. The polyethylene fiber is very cut resistant, but the knitted construction of the glove does not provide needlestick protection for the wearer.

The three surgeon's gloves described above degrade the tactility of the surgeon and do not provide needlestick protection. The weight of the metal knit and metal mesh gloves can accelerate fatigue during long surgical procedures.

A wide variety of protective gloves are also known in the art, each of which is designed for its own particular purpose. For example, U.S. Pat. No. 4,416,026 (Smith) issued on Nov. 22, 1983, discloses a multi-purpose mechanic's glove. This glove can be constructed of leather, heat-resistant materials, coated fabrics or combinations of these materials. The glove includes padding to protect the back of the hand, a removable gauntlet which may be joined to the glove with Velcro tape, slide actuated fasteners, straps or buttons, and a plurality of holes in the fingertip and palm areas of the glove. The glove provides a workman with hand protection and also allows him to feel the tools or work parts being handled.

U.S. Pat. No. 4,507,807 (Karkanen) issued on Apr. 2, 1985, discloses a work glove finger structure. The glove is constructed from a fabric coated with a suitable material such as neoprene or nitrile butyl rubber. High sensitivity glove tips are attached to a loose-fitting glove by sewing, vulcanizing or gluing. The high-sensitivity tips are made of neoprene or nitrile butyl rubber and are used at the thumb, index finger and middle finger. A high-friction band of silicone rubber is attached within the finger stall of the glove or molded in the high-sensitivity fingertip covering. The band provides a means for keeping the thin rubber fingertip drawn taut over the fingerprint area to assure improved tactility for the glove wearer.

U.S. Pat. No. 4,624,016 (Luevano) issued on Nov. 25, 1986, discloses an athletic glove with built-in cushioning. A leather glove with a cushion layer and innermost leather layers sewn inside the glove's palm to capture the cushioning material is disclosed. The athletic glove provides impact protection to the wearer's palm.

U.S. Pat. No. 2,309,476 (Patterson, Jr.) issued on Jan. 26, 1943, discloses a glove constructed of leather. The palm side of the glove is formed of two layers of leather cemented together. The inner layer is perforated prior to cementing the outer layer. The cemented layer assembly is then perforated in selected regions for ventilation of the wearer's hand. A partial vacuum results due to the inner layer perforations between the hand and the glove, improving the wearer's grip.

U.S. Pat. No. 3,387,306 (Korey) issued on Jun. 11, 1968, discloses a golf glove constructed of kid's skin, calf skin or kangaroo skin. The glove is assembled of leather by stitching. The glove covers the entire surface of the wearer's hand with the exception of the exposure of the thumb extending from just below the knuckle and exposure of the index finger extending from just below the second knuckle from the fingertip. The glove wearer's sense of touch is improved by the absence of glove coverage of portions of the thumb and index finger. The wearer can use the glove with appropriate golf clubs for both driving and putting without removing the glove.

The foregoing are examples of gloves known in the art which exhibit one or more features which may be useful to medical personnel wearing gloves to prevent accidents when handling needles. However, none of these gloves are satisfactory for use by medical personnel who must palpate to locate a suitable blood vessel and also have sufficient protection for their hands to avoid an accidental needle prick.

Accordingly, there is a need in the art for an improved glove design and method for making such a glove which may be used by medical personnel when handling needles to prevent accidental injuries which might result in exposure to infectious diseases.

SUMMARY OF THE INVENTION

The present invention relates to a glove for use by medical personnel to protect them from accidental injuries when handling needles and which is adapted to cover substantially the entire hand from the wrist to the fingertips. The glove includes a first layer of flexible material having a pore size which is smaller than the diameter of a needle and which forms a glove including four finger stalls and a thumb stall. The first layer optionally also includes at least two openings, one in the fingerprint area of the index finger stall and the second in the fingerprint area of the middle finger stall. The glove further includes a second layer of flexible material having a pore size which is smaller than the diameter of a needle and is attached to selected areas of the first layer of material to provide the selected areas with sufficient thickness to prevent needle penetration under normal conditions encountered when handling needles.

The selected areas to which the second discreet layer is attached preferably includes all of the thumb stall and lateral sides of both the index finger stall and middle finger stall. Preferably, the second discreet layer for each finger stall covering the lateral sides extends across the finger tip and is sewn to the first layer across a fingernail region of the finger stall. Thus, the fingerprint area of the finger stall up to the fingernail region is not covered by the second layer and thus maintains maximum tactility.

In order to further protect the user, the backsides of a first distal joint portion of the index finger stall and the middle finger stall also comprises part of the selected areas to be covered by the second discreet layer.

A V-opening is also preferably provided on a back side of the first discreet layer extending to a knuckle region. This V-opening facilitates the donning of the glove by the user. Then, at least two distinct fastening means are provided for adjustably fastening one side of the V-opening to the other side. With these two distinct fastening means, the glove width is easily adjustable at each fastening means to suit the needs of the user.

If additional protection is provided, a third discreet layer is preferably provided between the first and second layers of the thumb stall and the adjacent lateral side of the index finger. This third discreet layer is preferably a corrugated metal foil. The metal foil is preferably one-half to two mil stainless steel and can be provided in all the selected areas between the first layer and second layer if desired.

In a second aspect, the present invention relates to a method for making a sterile protective glove for use by medical personnel to protect them from accidental injuries when handling needles. The first step of the method provides a glove-shaped first layer of flexible material having a pore size which is smaller than the diameter of a needles and includes four finger stalls and a thumb stall. Then, a second layer of flexible material having a pore size smaller than the diameter of a needle is attached to selected areas of the first layer of material and the glove is sterilized. The sterilization step may be carried out by ethylene oxide gas permeation.

In a third aspect of the invention, a disinfecting solution is applied to the glove. The disinfecting solution can be a sporicidal in which the glove is immersed, or an isopropyl alcohol or hexachlorophene solution applied to the exterior surfaces of the glove.

It is the primary object of the present invention to provide a protective glove for use by medical personnel when handing needles which will prevent an accidental needle prick.

It is also an object of the present invention to provide a protective glove for use by medical personnel when handling needles which does not impair the tactility of the wearer's hand during use.

It is a further object of the present invention to provide a glove for use by medical personnel when handling needles which is relatively inexpensive and provides satisfactory protection from needle injuries.

It is a still further object of the present invention to provide a glove for use by medical personnel when handling needles which is sterilizable and which may be reused and resterilized.

It is yet another object of the present invention to provide a method for making a sterile protective glove for use by medical personnel when handling needles.

These and other objects of the present invention will be apparent to one of ordinary skill in the art from the detailed description which follows.

DETAILED DESCRIPTION OF THE PREFERRED EMBODIMENTS

Figures 1, 2, 3:
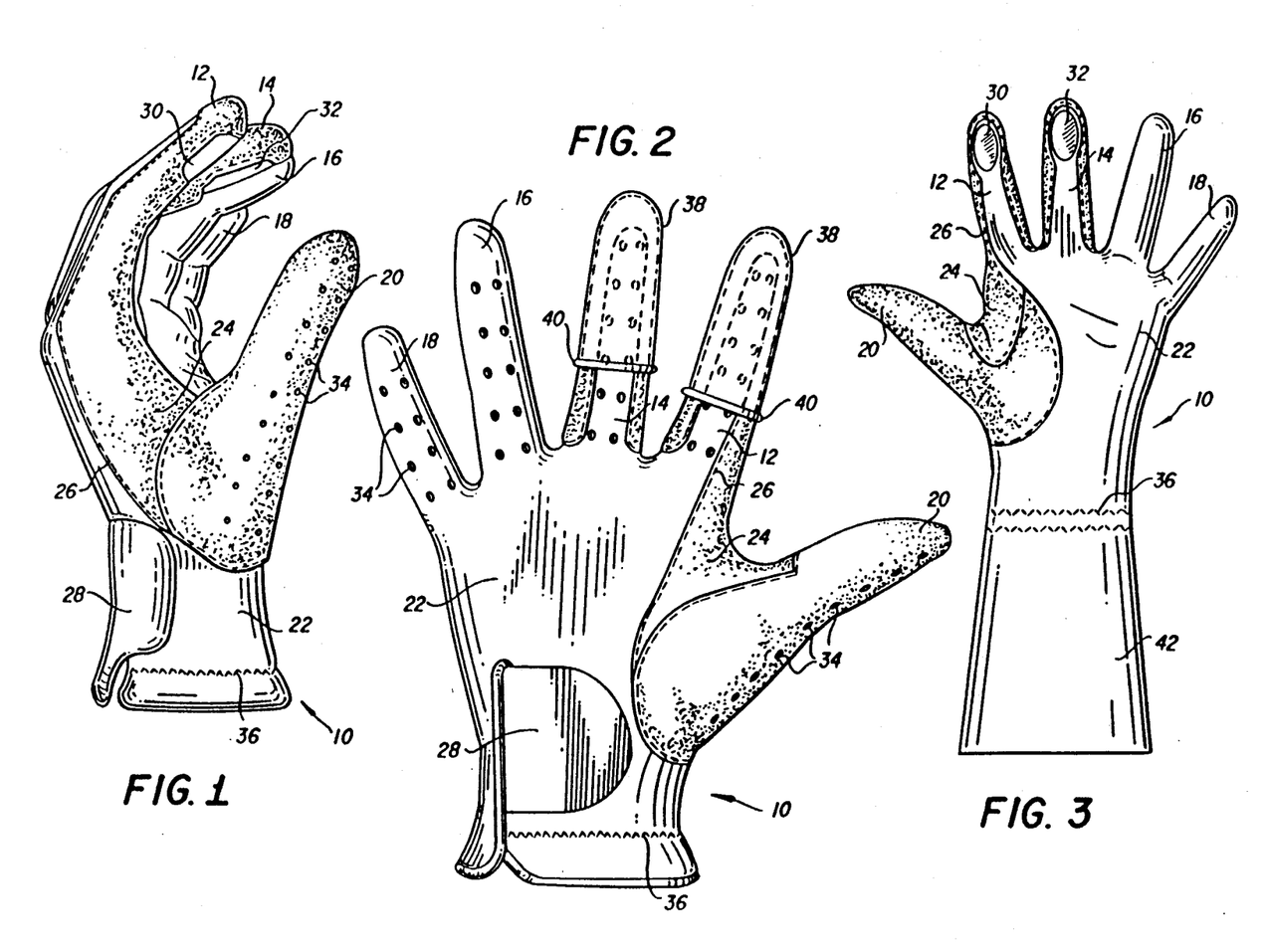
FIG. 1 is a perspective side view of one embodiment of a glove in accordance with the present invention.
FIG. 2 is a perspective view of the back side of a glove in accordance with the present invention, including optional finger cots on the middle and index fingers.
FIG. 3 is a perspective view of the palm side of a glove in accordance with the present invention, including an option gauntlet.

Referring now to FIG. 1, there is shown a side plan view of a protective glove in accordance with the present invention. Glove 10 includes four finger stalls: index or first finger stall 12, middle finger stall 14, third finger stall 16, and pinky finger stall 18. Glove 10 also includes thumb stall 20. Glove 10 is fabricated from a first layer 22 of flexible material and includes a second layer 24 of flexible material attached to selected portions of first layer 22 by any suitable means such as stitching 26. Glove 10 also includes fastening means 28 which is used to open and close the wrist portion of glove 10 to make it easier to take off and put on the user's hand.

Finally, glove 10 includes two optional openings therein. The first opening 30 is located in the fingerprint portion of index finger stall 12, and the second opening 32 is located in the fingerprint portion of middle finger stall 14. First and second openings 30 and 32 are present to improve the tactility of the user's hand when wearing the glove since first and second openings 30 and 32 allow direct contact between the user's hand and anything that is being touched.

Optionally, glove 10 may also include ventilation openings 34 to allow air to flow into the glove and thereby minimize sweating and discomfort. Further, the preferred glove 10 includes an area of elasticized stitching 36 near the base of the glove in order to provide a snug fit around the user's wrist while at the same time allowing easy entry and exit from the glove.

On FIG. 2 is shown a backside view of glove 10 in accordance with the present invention wherein like elements are designated by like numerals. The embodiment shown in FIG. 2 also includes a pair of finger cots 38 fitted over index finger stall 12 and middle finger stall 14 respectively. Finger cots 38 may be employed to prevent direct contact between the user's fingertips through first and second openings 30, 32 and the patient. Finger cots 38 may be made of a thin elastomeric material in order to preserve maximum tactility of the gove wearer's fingertips. Finger cots 38 preferably include elastic ring 40 which fits tightly about the fingers of the glove wearer in order to maintain finger cots 38 on the fingers as well as to provide a seal between glove 10 and finger cots 38 to thereby prevent contamination from the glove wearer's fingertips from escaping outside finger cots 38. As an alternative to finger cots 38, other gloves such as rubber or latex may be worn over the glove of the present invention to preserve sterility.

Instead of finger cots 38, a surgeon or the like may desire to use glove 10 together with single or double gloving of latex to assure sterility. When double-gloving, a latex sterile glove is donned followed by the donning of glove 10. Then, the second or outer most latex sterile glove would be pulled over glove 10 to prevent all contact with the patient's body fluids. In the event of an accidental needlestick, the patient's body fluids would then penetrate the outermost latex glove and possibly contaminate glove 10. However, the initial latex glove will continue to provide protection from fluid contact with the surgeon's skin.

If glove 10 contains palpitation windows 30 and 32, there would still be two thicknesses of latex separating the surgeons finger tips from the patient's body contact surface. This would thus provide improved needlestick protection, while allowing for tactility which is greater in comparison to the currently available gloves which involve two thicknesses of latex plus the thickness of a knitted or woven glove material. It should also be appreciated that glove 10 easily complies with the folds and creases of the skin covering the hand and thus assumes a more natural folding than the knitted or woven wire mesh gloves of the prior art which have a tendency to gather or pucker when clasping the hand. Glove 10 is also lightweight and thus should not cause hand fatigue in comparison with the heavier metal mesh or knitted gloves of the prior art.

Referring now to FIG. 3, there is shown a palm side view of a third embodiment of a glove in accordance with the present invention. Again, like numerals designate like elements. This embodiment of glove 10 includes a gauntlet 42 attached thereto. Gauntlet 42 is an optional modification to glove 10 which improves the glove's ability to be adapted to a sterile environment. Gauntlet 42 may be folded up as a cuff such that glove 10 may be donned in a sterile environment without the user touching any part of the outside of glove 10 and thereby contaminating it.

Figure 4:
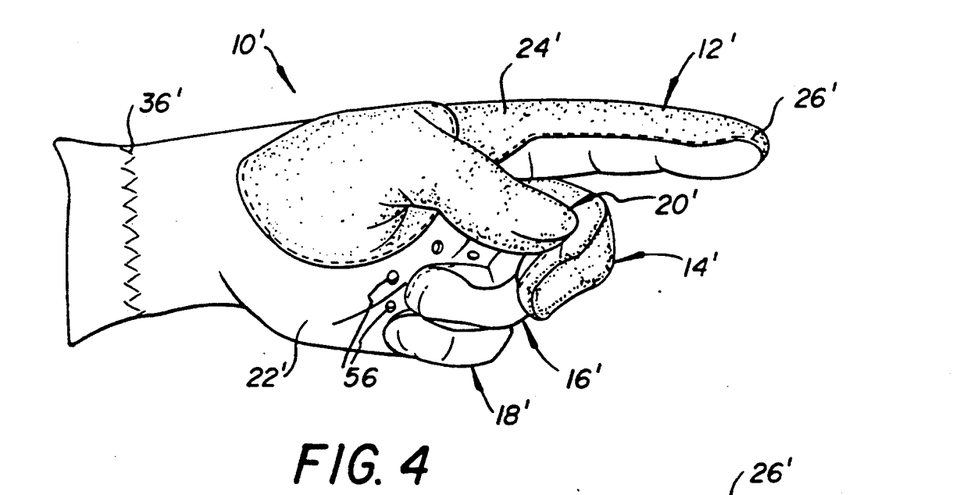
FIG. 4 is a perspective side view of an alternative embodiment of a glove in accordance with the present invention.

Depicted in FIG. 4 is an alternative embodiment of glove 10' which is broadly similar to glove 10 described above. Thus, the similar elements of glove 10' will be identified with the same numerals as used for glove 10, but with an "'" after the number. In glove 10', both first finger stall 12' and middle thereof. In particular, the coverage of second layer 24' at the tips of the fingers as well as the line of joining of the two portions of first layer 22' which come together to form each finger stall 12' and 14' has been moved so that stitching 26' is located in the fingernail region rather than the central plane of finger stalls 12' and 14'. By locating stitching 26' in this manner, a free, unobstructed, smooth layer of leather across the finger tips of the index and middle fingers is provided so that a surgeon utilizing glove 10' has increased tactility when clasping the patient's flesh or the like. Stitching 26' is also preferably located in the fingernail region for stalls 16', 18' and 20' as well.

Figure 6:
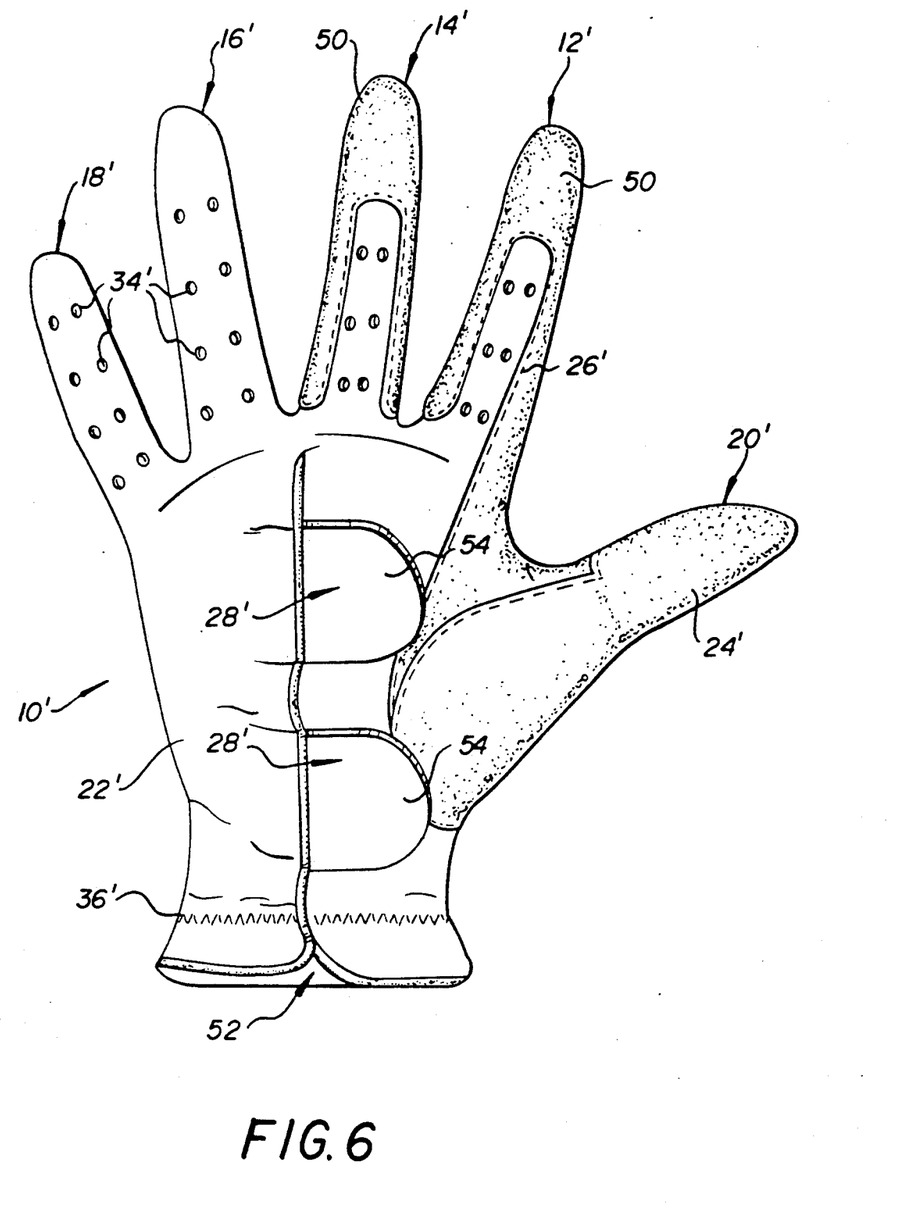
FIG. 6 is perspective view of a backside of the glove depicted in FIG. 4.

Glove 10' has also been provided with a back side covering 50 for both first finger stall 12' and middle finger stall 14' as best shown in FIG. 6. Back side covering 50 essentially covers the first distal joint to provide additional protection from needle penetration. This is particularly desirable for use by an anesthesiologist when inserting an IV catheter.

Glove 10' also includes a modified fastening means 28'. Fastening means 28' includes a V-opening 52 which extends in length to the knuckle region of the hand. The opening 52 thus helps to facilitate the wearer donning the glove. Then, two velcro flaps 54 spaced along V-opening 52 are used to fasten the two sides of V-opening 52 together. Of course, more than two such velcro flaps could be used if desired. By using velcro flaps 54, a proper fit of glove 10' at the wrist and also about the palm or width of the hand to suit the needs of the user is achieved. Fastening means 28' also permits the wearer to compensate for glove leather stretch caused by the wearer's perspiration.

Figure 5:
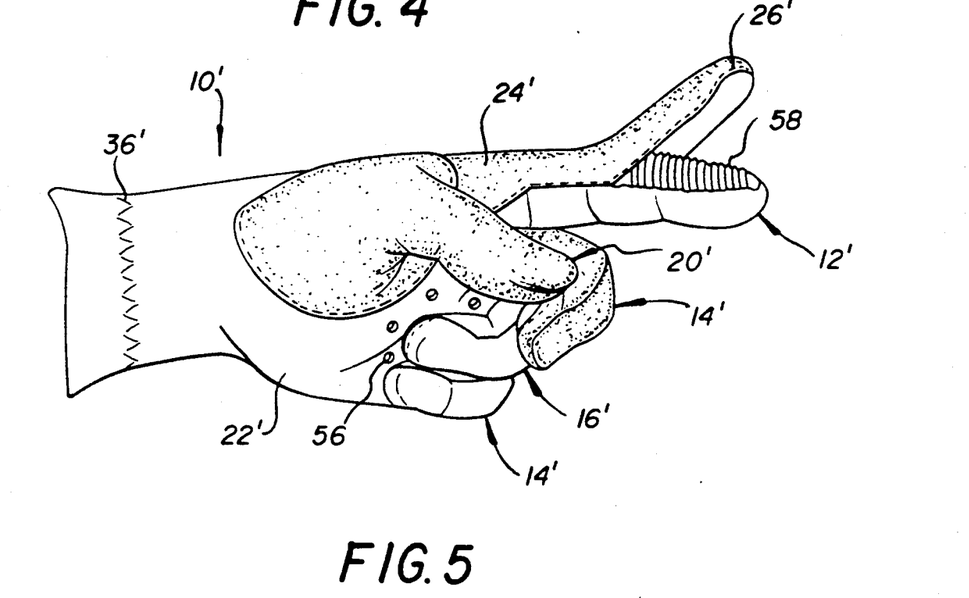
FIG. 5 is a perspective side view of the glove depicted in FIG. 4 with a portion of a second layer lifted up.

As shown in FIG. 6, glove 10' includes ventilation openings 34' on the back side of stalls 12', 14', 16', and 18' (but not on thumb stall 20' as in the embodiment depicted in FIGS. 1 and 2). In addition, ventilation openings 56 have been provided for glove 10' across the palm thereof as shown in FIGS. 4 and 5. Openings 34' and 56 are optional, but help to improve the post operation drying rate of the glove after becoming wet from hand perspiration.

The protective glove of the present invention is preferably constructed of cabretta leather (a soft leather from the skins of hairy sheep), although other materials such as calfskin, buckskin, kangaroo leather and polyurethane resin impregnated fabric may be employed. The cabretta leather is chrome-tanned naked leather having a natural platinum gray color and maintaining a supple and soft feel. The leather is reduced to a uniform thickness of one and one-quarter ounces per square foot and thinner in selected areas to impart tactility to the wearer's fingers.

The glove is sewn or fabricated of single-ply leather with a second leather ply tailored to fit, cut to size and attached by sewing in selected areas that are deemed vulnerable to needlesticks as shown in FIGS. 1–6. The two-ply construction of the glove is shown along the side of the index and middle finger continuing over the snuff-box region of the hand and fully encompassing the thumb stall. Two-plys of leather have been demonstrated to provide needlestick protection under the normal thrusting forces to resheath a needle. Many needlestick accidents occur when medical personnel attempt to resheath the needle. Accidents have occurred whereby the needle enters the sheath at an angle and penetrates the plastic sheath and pricks the user. Also, accidents have occurred whereby the needle misses the sheath entirely and sticks the sides of the finger, the thumb or the snuff-box region of the hand. The two-ply leather protected areas of the glove of the present invention appear to be the most prevalent areas of needlestick occurrence. However, the glove design could also have areas of reinforcement for all of the fingers and other hand locations if deemed advisable and is not to be considered to be limited to the precise form disclosed in the drawings.

The glove material is soft, supple and allows the wearer to grip, feel and grasp objects. The glove's index and middle fingers each optionally have openings at their extremities to expose the fingerprint areas of the wearer. As a result, the wearer can palpate a patient by direct contact with a patient's skin if desired. If prevention of patient contact is required, rubber or vinyl latex finger cots may be placed over the openings as shown in FIG. 2 with the rolled free edge of the finger cot located between the second and third joint from the tip of the fingers. The finger cots rolled edge allows a compressive force to be applied to the glove's exterior thereby maintaining a taut, drawn latex membrane over the fingerprint region to assure excellent tactility of the wearer.

The leather material is porous to a minimal degree and therefore will absorb liquids and become stained when contaminated with blood. In a preferred embodiment, the glove color is chosen to closely match the color of a dried blood stain to minimize the discoloration of the glove in use. A leather treatment such as a silicone finish may impart anti-wetting properties to the surface of the leather. Such a finish would prevent bloodstain discoloration and still maintain the porosity of the leather permitting it to breathe.

An important feature of the glove of the present invention is that it is sterilizable and useful under sterile conditions. Two different sterilization procedures and two surface disinfection procedures have been successfully applied to the glove of the present invention. The first, and most preferred procedure, utilized ethylene oxide gas at 130 degree fahrenheit. The glove is permeated by ethylene oxide gas for a period of 1¾ hours up to a four hour maximum dwell time, followed by a twelve hour room-temperature aeration. This sterilization process appeared to have a minimal effect on the coloration, size and flexibility of the glove leather. This procedure, although expensive, is a satisfactory approach to glove sterilization.

A second sterilization procedure was also found to be satisfactory, although less preferred than the ethylene oxide procedure. This procedure involves immersion of a leather glove in a sporicidal solution such as SPORICIDIN (a solution of 0.13% glutaraldehyde-phenate complex, alkaline solution diluted 1 part solution to 16 parts sterile water). This procedure had a minimal effect on the color of the leather, the size of the glove finger and the feel of the leather. The 10 to 15 minute time of glove immersion in the glutaraldehyde solution followed by a thorough rinsing and drying will sterilize the glove. A glove test sample was immersed for 24 hours followed by rinsing and drying. This sterilization cycle is equivalent to approximately 100 glove immersions at 10–15 minutes per cleaning cycle, thus indicating that the glove cold be sterilized by repeated immersion and drying cycles and still maintain its serviceability. However, this procedure is less preferred since residual SPORICIDIN solution must be thoroughly removed from the glove to prevent skin irritation to the wearer of the glove.

A disinfection procedure was developed to disinfect the outer surface of the glove while being worn by a medical specialist. A hexachlorophene foam disinfectant such as SEPTISOL foam made by Vestal Lab of St. Louis, Missouri can be applied by the glove wearer using the manufacturer's instructions for disinfecting the skin. This procedure permits glove contact area disinfection for use in field emergencies and for multi-patient care without the time delay required by ethylene oxide gas or sporicidal solution immersion sterilization procedures. Isopropyl alcohol (70% in water) is also usable as a suitable surface disinfectant.

In use, the glove is typically used by a surgeon or an intravenous therapy nurse. Generally for such a nurse, the nurse must locate a suitable blood vessel in the patient's limb, normally the arm, by palpating the patient which requires maximum tactility at the fingerprint area of the index and middle fingers. Upon location of a suitable blood vessel, the nurse inserts a hypodermic needle through the skin and into the subject vessel to inject a fluid or withdraw the patient's blood which, in either case, contaminates the needle. The glove of the present invention prevents the wearer from accidentally penetrating his or her skin when handling such contaminated needles, and thus minimizes exposure to highly-communicable diseases such as hepatitis B and AIDS. When used by surgeons, the glove of the present invention also allows maximum tactility while preventing accidental needlestick penetration. Further, by being lightweight, fatigue of the surgeon's hands is reduced.

The glove could also be utilized by hematologists and laboratory technicians, where glassware containing blood samples is processed. Accidents have occurred whereby glassware fractured in the technician's hand and glass chards contaminated with diseased blood penetrated the technician's skin. The glove of the present invention provides some limited protection from glass chard penetration.

In a sterile environment, the glove design of the present invention can be modified with a gauntlet 42 as shown in FIG. 3 in order to permit the wearer to don the glove in the sterile environment. The gauntlet would be folded upwardly when the glove is sterilized and packaged to form a cuff and the user would handle only the cuff when donning the glove. Once the glove is on, the cuff would be pulled down to remain uncontaminated. The glove may be worn on either hand or both hands if desired to provide limited cut protection, glass chard penetration resistance and needlestick protection.

Another method of needlestick protection in accordance with the present invention would utilize a needle impenetrable insert layer 58 placed between first layer 22' and second layer 24' of leather in the area to be reinforced as shown in FIG. 5. This reinforcement ply would be chosen for its needlestick protection and also for its ability to flex, allowing the fingers of the wearer a minimum restraint in performance of their normal functions. Suitable needle impenetrable insert layers would be materials having very small pore sizes which would not allow penetration of a needle without significant forces being exerted.

Depicted in FIG. 5 is one suitable layer 58 which is formed from a corrugated metal foil of one-half to two mil thickness stainless steel. This metal foil is captured between layers 22' and 24'. By corrugating the metal foil, this allows layer 58 to conform to shapes and direction changes which occur when the hand or fingers of the user are flexed. At a minimum, metal layer 58 is provided to protect the thumb side of the index finger, the anatomical snuff-box region, and the vulnerable side or back side of thumb stall 20'. If desired, metal layer 58 can also be provided at all locations of second layer 24' so that wherever second layer 24' was provided there would be an underlying metal layer 58.

The following examples are provided to illustrate the fabrication of a needlestick protective glove in accordance with the first embodiment of the present invention.

EXAMPLE

Seven identical gloves of white cabretta leather were purchased. Six of these gloves were sterilized using ethylene oxide gas, using the sterilization facilities of a local hospital. The glove tests were conducted with guidelines for each of the gloves to be sterilized a different number of cycles ranging from 1 cycle to 24 cycles. One glove, identical to the 6 sterilized gloves, was used as a control sample and did not undergo sterilization, thus permitting comparison of fit, color, feel and appearance to determine if the sterilization procedure degraded these properties. Each sterilization cycle involved exposure to ethylene oxide gas at a temperature of 130 degree F, for one and three-fourths to a maximum of four hours followed by an aeration cycle of twelve hours in a circulating air environment.

Glove 1 was subjected to one ethylene oxide sterilization cycle. The glove leather appeared soft, supple and without any noticeable color change. The fit of the glove appeared slightly more snug than the control sample as a result of the sterilization processing. The sheen of the glove appeared to have been lost after the one cycle as compared with the control sample glove.

Glove 2 was subjected to four ethylene oxide sterilization cycles. The glove leather appeared soft and supple with a minimum of discoloration. The glove shrank as evidenced by the amount of Velcro flap overlap and by the feel of the glove's fit on the hand.

Glove 3 was subjected to eight ethylene oxide sterilization cycles. The glove leather remained soft and supple with minimal color change. The glove shrank in size as indicated by the Velcro flap overlap and the glove's fit appeared more snug, but was entirely satisfactory.

Glove 4 was subjected to twelve ethylene oxide sterilization cycles. The leather appeared soft and supple, some glove shrinkage had occurred but the glove had a satisfactory fit. The Velcro flap did not overlap as far as the control glove, indicating some leather shrinkage had occurred.

Glove 5 underwent 18 ethylene oxide sterilization cycles. The leather still appeared soft and supple. The ring and little finger of the glove had one spot each on the palm side where the leather appeared stiffer. These two spots may have been contaminated during the glove making procedure or packaging operations. The leather color appeared slightly less white than the control sample. The glove had shrunk in size as indicated by the Velcro flap overlap and felt snug on the hand when compared with the control sample glove. The fit of the glove was still entirely satisfactory.

Glove 6 underwent 24 ethylene oxide sterilization cycles. The color of the leather had only slightly yellowed as compared with the control sample and the leather had remained soft and supple. The glove had shrunk as indicated by the amount of Velcro flap overlap and the fit of the glove compared with the control sample. However, the fit was still entirely satisfactory.

The ethylene oxide sterilization cycle appeared to have a slight effect upon the leather of the glove with increasing shrinkage as related to the number of sterilization cycles. All of the gloves remained substantially white and the fit was entirely adequate. It is anticipated that the gloves will stretch slightly with wear and these gloves were not worn at any time other than the initial trial fit prior to sterilization. Therefore, they were not subjected to hand oils and perspiration as would be expected on normal usage.

The foregoing description of embodiments of the invention has been presented for purposes of illustration and description only. Many modifications and variations will be apparent to one of ordinary skill in the art in light of the above teachings. Accordingly, the scope of the invention is to be defined by the claims appended hereto.

We claim:

1. A glove for use by medical personnel to protect them from accidental injuries when handling needles which is adapted to cover substantially the entire hand from the wrist to the fingertips which comprises:

a first discrete layer of a flexible material having a pore size which is smaller than the diameter of a needle and which forms a glove including index, middle, third and pinky finger stalls and a thumb stall;

a second discrete layer of flexible material having a pore size which is smaller than the diameter of a needle, said second layer being permanently sewn to selected areas of said first layer of material to provide said selected areas with sufficient thickness to prevent needle penetration under normal conditions encountered when handling needles, said selected areas comprising all of said thumb stall and lateral sides of both said index finger stall and said middle finger stall, said second discrete layer for each finger stall covering said lateral sides extending across the fingertip and being sewn to said first layer across a fingernail region of said finger stall wherein a fingerprint area of said finger stall up to the finger nail region is not covered by said second layer; and a third discrete layer formed of a corrugated metal foil provided between said first and second layers of said thumb stall and of the adjacent lateral side of said index finger stall.

2. A glove as claimed in claim 1 wherein said selected areas also includes back sides of a first distal joint portion of said index finger stall and said middle finger stall.

3. A glove as claimed in claim 1 and further including: a V-opening provided on a backside of said first discrete layer extending to a knuckle region to facilitate donning of the glove; and at least one side of said V-opening to the other side such that the glove width is adjustable at each fastening means to suit the needs of the user.

4. A glove as claimed in claim 1 and further including at least two openings in said first layer, one in the fingerprint area of said index finger stall and the second in the fingerprint area of said middle finger stall.

5. A glove as claimed in claim 1 wherein said selected areas further comprise an extension of said second layer of said thumb stall and adjacent lateral side of said index finger stall to the snuff box region of the glove.

6. A glove as claimed in claim 1 and further comprising a plurality of ventilation perforations on a back side of said first layer of the glove.

7. A glove as claimed in claim 6 and further comprising a plurality of ventilation perforations on a palm side of said first layer of the glove.

8. A glove as claimed in claim 1 wherein the glove is sterilized, and further including a gauntlet to permit the user to don the glove in a sterile environment.

9. A glove for use by medical personnel to protect them from accidental injuries when handling needles which is adapted to cover substantially the entire hand from the wrist to the fingertips which comprises:

a first discrete layer of a flexible material having a pore size which is smaller than the diameter of a needle and which forms a glove including index, middle, third and pinky finger stalls and a thumb stall;

a second discrete layer of flexible material having a pore size which is smaller than the diameter of a needle, said second layer being permanently attached to selected areas of said first layer of material to provide said selected areas with sufficient thickness to prevent needle penetration under normal conditions encountered when handling a needles, said selected areas comprising all of said thumb stall, lateral sides of both said index finger stall and said middle finger stall, and back sides of a first distal joint portion of both said index finger stall and said middle finger stall; and a third discrete layer formed of a corrugated metal foil provided between said first and second layers of said thumb stall and of the adjacent lateral side of said index finger stall.

10. A glove as claimed in claim 9 and further including: a V-opening provided on a backside of said first discrete layer extending to a knuckle region to facilitate donning of the glove; and at least two distinct fastening means for adjustably fastening one side of said V-opening to the other side such that the glove width is adjustable at each fastening means to suit the needs of the user.

11. A glove as claimed in claim 9 and further including at least two openings in said first layer, one in the fingerprint area of said index finger stall and the second in the fingerprint area of said middle finger stall.

12. A glove as claimed in claim 9 wherein said selected areas further comprise an extension of said second layer of said thumb stall and adjacent lateral side of said index finger stall to the snuff box region of the glove.

13. A glove as claimed in claim 9 and further comprising a plurality of ventilation perforations on a back side of said first layer of the glove.

14. A glove as claimed in claim 13 and further comprising a plurality of ventilation perforations on a palm side of said first layer of the glove.

15. A glove as claimed in claim 9 wherein the glove is sterilized, and further including a gauntlet to permit the user to don the glove in a sterile environment.

16. A glove for use by medical personnel to protect them from accidental injuries when handling needles which is adapted to cover substantially the entire hand from the wrist to the fingertips which comprises:

a first discrete layer of a flexible material having a pore size which is smaller than the diameter of a needle and which forms a glove including index, middle, third and pinky finger stalls and a thumb stall;

a second discrete layer of flexible material having a pore size which is smaller than the diameter of a needle, said second layer being permanently attached to selected areas of said first layer of material to provide said selected areas with sufficient thickness to prevent needle penetration under normal conditions encountered when handling needles, said selected areas comprising all of said thumb stall and lateral sides of both said index finger stall and said middle finger stall;

a third discrete layer formed of a corrugated metal foil provided between said first and second layers of said thumb stall and of the adjacent lateral side of said index finger stall;

a V-opening provided on a backside of said first discrete layer extending to a knuckle region to facilitate donning of the glove; and at least two distinct fastening means for adjustably fastening one side of said V-opening to the other side such that the glove width is adjustable at each said fastening means to suit the needs of the user.

17. A glove as claimed in claim 16 and further including at least two openings in said first layer, one in the fingerprint area of said index finger stall and the second in the fingerprint area of said middle finger stall.

18. A glove as claimed in claim 16 wherein said selected areas further comprise an extension of said second layer of said thumb stall and adjacent lateral side of said index finger stall to the snuff box region of the glove, 19. A glove as claimed in claim 16 and further comprising a plurality of ventilation perforations on a back side of said first layer of the glove.

20. A glove as claimed in claim 19 and further comprising a plurality of ventilation perforations on a palm side of said first layer of the glove.

21. A glove as claimed in claim 16 wherein the glove is sterilized, and further including a gauntlet to permit the user to don the glove in a sterile environment.

22. A glove for use by medical personnel to protect them from accidental injuries when handling needles which is adapted to cover substantially the entire hand from the wrist to the fingertips which comprises:
- a first discrete layer of a flexible material having a pore size which is smaller than the diameter of a needle and which forms a glove including index, middle, third and pinky finger stalls and a thumb stall;
- a second discrete layer of flexible material having a pore size which is smaller than the diameter of a needle, said second layer being permanently attached to selected areas of said first layer of material to provide said selected areas with sufficient thickness to prevent needle penetration under normal conditions encountered when handling needles, said selected areas comprising all of said thumb stall and lateral sides of both said index finger stall and said middle finger stall; and
- a third discrete layer formed of a corrugated metal foil provided between said first and second layers of said thumb stall and of the adjacent lateral side of said index finger stall.

23. A glove as claimed in claim 22 wherein said third discrete layer is one-half to two mil stainless steel.

24. A glove as claimed in claim 22 wherein said third discrete layer is provided between said first layer and said second layer in all said selected areas.

25. A glove as claimed in claim 22 and further including at least two openings in said first layer, one in the fingerprint area of said index finger stall and the second in the fingerprint area of said middle finger stall.

26. A glove as claimed in claim 22 wherein said selected areas further comprise an extension of said second layer of said thumb stall and adjacent lateral side of said index finger stall to the snuff box region of the glove.

27. A glove as claimed in claim 26 wherein said third discrete layer is provided between said first layer and said second layer in all said selected areas.

28. A glove as claimed in claim 22 and further comprising a plurality of ventilation perforations on a back side of said first layer of the glove.

29. A glove as claimed in claim 28 and further comprising a plurality of ventilation perforations on a palm side of said first layer of the glove.

30. A glove as claimed in claim 22 wherein the glove is sterilized, and further including a gauntlet to permit the user to don the glove in a sterile environment.

* * * * *